United States Patent [19]

Amento et al.

[11] Patent Number: 5,108,989
[45] Date of Patent: Apr. 28, 1992

[54] METHOD OF PREDISPOSING MAMMALS TO ACCELERATED TISSUE REPAIR

[75] Inventors: Edward P. Amento, Portola Valley; L. Steven Beck, Los Altos, both of Calif.

[73] Assignee: Genentech, Inc., South San Francisco, Calif.

[21] Appl. No.: 504,495

[22] Filed: Apr. 4, 1990

[51] Int. Cl.$^5$ .............................................. A61K 37/02
[52] U.S. Cl. ......................................... 514/12; 514/21
[58] Field of Search ...................................... 514/12, 21

[56] References Cited

FOREIGN PATENT DOCUMENTS 0375127 6/1990 European Pat. Off. .
WO9100103 3/1991 PCT Int'l Appl. .

OTHER PUBLICATIONS

Pierce et al., J. Cell Biol., 109: 429–440 (1989).
Ksander et al., Ann. Surg., 211 (3):288–294 1990).

*Primary Examiner*—Howard E. Schain
*Assistant Examiner*—Choon Koh
*Attorney, Agent, or Firm*—Janet E. Haska

[57] ABSTRACT

A method of predisposing a mammal to accelerated tissue repair is provided. This method comprises systemically administering to the mammal, prior to its exposure to tissue damage, an effective amount of TGF-$\beta$. Preferably, the TGF-$\beta$ is administered no more than about 24 hours prior to exposure to tissue damage.

9 Claims, 4 Drawing Sheets

```
                             1          10              20             32              40           50
Hu TGF-β  1   MPPSGLRLLPLLPLLWLLV-LTPGPPAAGLSTCKTIDMELVKRKRIEAIR
Hu TGF-β  2   MHYCVLSAFLILHLV---TVAL------S-LSTCSTLDMDQFMRKRIEAIR
Hu TGF-β  3   --MHLQRALVVLALLNFATVSL------S-LSTCTTLDFGHIKKRVEAIR 60             70             80             90
Hu TGF-β  1   GQILSKLRLASPPSQGE-VP-PGPLPEAVLALYNSTRDRVAGESAEPE-PE
Hu TGF-β  2   GQILSKLKLTSPP----EDYPEPEEVPEVISIYNSTRDLL--QEKASR-RA
Hu TGF-β  3   GQILSKLRLTSPP---EPTV-MTHVPYQVLALYNSTRELL--EEHGER-KE
Ck TGF-β  4   ------------------------------------M--DPMSIGPK- 100            110            120            130
Hu TGF-β  1   P------EADYYAKEVTRVLMV----ETHNEIYDKFKQSTHSIYMFFNTS
Hu TGF-β  2   AACERERSDEEYYAKEVYKIDMPPFFPS-EHAIPPTFYRPY-FRIVRFDVS
Hu TGF-β  3   EGCTQENTESEYYAKEIHKFDMIQGLAE-HNELAVCPKGIT-SKVFRFNVS
Ck TGF-β  4   -SCG---------------------GSPW-RPP-GTAPWSIG-SR--RATAS 140            150            160            170
Hu TGF-β  1   EL------RE-AVPEPVLLS-RAELRLLRLKL----KV-EQHVELYQ----
Hu TGF-β  2   A-------MEKNASNLV-KAEFRVFRLQNPK-ARVPEQRIELYQILKSK
Hu TGF-β  3   S-------VEKNRTNLF-RAEFRVLRVPNPS-SKRNEQRIELFQILRP-
Ck TGF-β  4   SSCSTSSRVRAEVGGRALLHRAELRMLRQKAAADSAGTEQRLELYQGYGN- 180            190            200            210            220
Hu TGF-β  1   KYSNNSWRYLSNRLLAPSDSPEWLSFDVTGVVRQWLSRGGEIEGFRLSAHC
Hu TGF-β  2   DLTSPTQRYIDSKVVKTRAEGEWLSFDVTDAVHEWLHHKDRNLGFKISLHC
Hu TGF-β  3   DEHIAKQRYIGGKNLPTRGTAEWLSFDVTDTVREWLLRRESNLGLEISIHC
Ck TGF-β  4   ----ASWRYLHGRSVRATADDEWLSFDVTDAVHQWLSGSELLGVFKLSVHC
Fg TGF-β  5   -------------------DEWMSFDVTKTVNEWLKRAEENEQFGLQPAC
```

FIG. 1A

```
                                   230           240           250
Hu  TGF-β  1   SC-------DSRDNTLQVDIN-GFTTGR------RGDLATI-----------
Hu  TGF-β  2   PCCTFVPSNNYIIPNKSEELEARFA-GIDGTSTYTSGDQKTIKSTRKKNSG
Hu  TGF-β  3   PCHTFQP-NGDILENIHEVMEIKFK-GVDNEDDHGRGDLGRLK----KQKDH
Ck  TGF-β  4   PCEMGPG-HADEMRISIEGFEQQ----------------RGDMQSIA----K-KHR
Fg  TGF-β  5   KCPT-PQ-AKDI-D--IEGFPAL-----------------RGDLASLSS--KEN---

260           270           280           290
Hu  TGF-β  1   HGMNRPFLLLMATPLERA-QH--LQSS----RHRRALDTNYCF--SSTEKNC
Hu  TGF-β  2   KT----PHLLLMLLPSYRL-ESQ---QTNRRKKRALDAAYCF--RNVQDNC
Hu  TGF-β  3   H---N-PHLILMMIPPHRL-DNPGQGGQ---RKKRALDTNYCF--RNLEENC
Ck  TGF-β  4   R--V-PYVLAMALPAERANE---LHSA---RRRRDLDTDYCFGPGTDEKNC
Fg  TGF-β  5   -TK--PYL--MIT-SMPAERIDTVTSS---RKKRGVGQEYCF--GNNGPNC 300           310           320           330           340
Hu  TGF-β  1   CVRQLYIDFRKDLGWKWIHEPKGYHANFCLGPCPYIWSLDTQYSKVLALYN
Hu  TGF-β  2   CLRPLYIDFRKDLGWKWIHEPKGYNANFCAGACPYLWSSDTQHSRVLSLYN
Hu  TGF-β  3   CVRPLYIDFRQDLGWKWVHEPKGYYANFCSGPCPYLRSADTTHSTVLGLYN
Ck  TGF-β  4   CVRPLYIDFRKDLQWKWIHEPKGYMANFCMGPCPYIWSADTQYTKVLALYN
Fg  TGF-β  5   CVKPLYINFRKDLGWKWIHEPKGYEANYCLGNCPYIWSMDTQYSKVLSLYN 350           360           370           380           390
Hu  TGF-β  1   QHNPGASAAPCCVPQALEPLPIVYYVGRKPKVEQLSNMIVRSCKCS
Hu  TGF-β  2   TINPEASASPCCVSQDLEPLTILYYIGKTPKIEQLSNMIVKSCKCS
Hu  TGF-β  3   TLNPEASASPCCVPQDLEPLTILYYVGRTPKVEQLSNMVVKSCKCS
Ck  TGF-β  4   QHNPGASAAPCCVPQTLDPLPIIYYVGRNVRVEQLSNMVVRACKCS
Fg  TGF-β  5   QNNPGASISPCCVPDVLEPLPIIYYVGRTAKVEQLSNMVVRSCNCS
```

METHOD OF PREDISPOSING MAMMALS TO ACCELERATED TISSUE REPAIR

BACKGROUND OF THE INVENTION

1. Field of the Invention

This invention relates to a method of predisposing mammals, especially humans, to accelerated tissue repair. More particularly, this invention is directed to a method of treating a mammal with transforming growth factor-beta before tissue injury to accelerate repair of the tissue.

2. Description of Related Disclosures

The beta transforming growth factors (TGF-$\beta$s) are multifunctional cytokines, produced by many types of cells, including hematopoietic, neural, heart, fibroblast, and tumor cells, that can regulate the growth and differentiation of cells from a variety of tissue origins (Sporn et al., *Science*, 233: 532 (1986)) and stimulate the formation and elaboration of various stromal elements.

There are at least five forms of TGF-$\beta$ currently identified, TGF-$\beta$1, TGF-$\beta$2, TGF-$\beta$3, TGF-$\beta$4, and TGF-$\beta$5. Suitable methods are known for purifying this family of TGF-$\beta$s from various species such as human, mouse, green monkey, pig, bovine, chick, and frog, and from various body sources such as bone, platelets, or placenta, for producing it in recombinant cell culture, and for determining its activity. See, for example, R. Derynck et al., *Nature*, 316:701–705 (1985); European Pat. Pub. Nos. 200,341 published Dec. 10, 1986, 169,016 published Jan. 22, 1986, 268,561 published May 25, 1988, and 267,463 published May 18, 1988; U.S. Pat. No. 4,774,322; Cheifetz et al, *Cell*, 48: 409–415 (1987); Jakowlew et al., *Molecular Endocrin.*, 2: 747–755 (1988); Dijke et al., *Proc. Natl. Acad. Sci. (U.S.A.)*, 85: 4715–4719 (1988); Derynck et al., *J. Biol. Chem.*, 261: 4377–4379 (1986); Sharples et al., *DNA*, 6: 239–244 (1987); Derynck et al., *Nucl. Acids. Res.*, 15: 3188–3189 (1987); Derynck et al., *Nucl. Acids. Res.*, 15: 3187 (1987); Derynck et al., *EMBO J.*, 7: 3737–3743 (1988)); Seyedin et al., *J. Biol. Chem.*, 261: 5693–5695 (1986): Madisen et al., *DNA*, 7: 1-B (198B): and Hanks et al., *Proc. Natl. Acad. Sci. (U.S.A.)*, 85: 79–82 (1988), the entire contents of these publications being expressly incorporated by reference.

The activated form of TGF-$\beta$1 is a homodimer formed by dimerization of the carboxy-terminal 112 amino acids of a 390 amino acid precursor (Derynck et al., *Nature*, supra). Recombinant TGF-$\beta$1 has been cloned (Derynck et al., *Nature*, supra) and expressed in Chinese hamster ovary cells (Gentry et al., Mol. Cell. Biol., 7: 3418–3427 (1987)).

TGF-$\beta$2 has a precursor form of 414 amino acids and is also processed to a homodimer from the carboxy-terminal 112 amino acids that shares approximately 70% homology with the active form of TGF-$\beta$1 (Marquardt et al., *J. Biol. Chem.*, 262: 12127 (1987)). TGF-$\beta$2 has been purified from porcine platelets (Seyedin et al., *J. Biol. Chem.*, 262: 1946–1949 (1987)) and human glioblastoma cells (Wrann et al., *EMBO J.*, 6: 1633 (1987)), and recombinant human TGF-$\beta$2 has been cloned (deMartin et al., *EMBO J.*, 6: 3673 (1987)).

TGF-$\beta$3, TGF-$\beta$4, and TGF-$\beta$5, which are the most recently discovered forms of TGF-$\beta$, were identified by screening cDNA libraries. The putative protein products of these three genes have not been isolated from natural sources, although Northern blots demonstrate expression of the corresponding mRNAs. Human and porcine TGF-$\beta$3 have been cloned and described previously (Derynck et al., *EMBO J.*, 7: 3737–3743 (1988), ten Dijke et al., *Proc. Natl. Acad. Sci. USA*, 85: 4715 (1988)). TGF-$\beta$4 and TGF-$\beta$5 were cloned from a chicken chondrocyte cDNA library (Jakowlew et al., *Molec. Endocrinol.*, 2: 1186–1195 (1988)) and from a frog oocyte cDNA library, respectively. The frog oocyte cDNA library can be screened using a probe derived from one or more sequences of another type of TGF-$\beta$. TGF-$\beta$4 mRNA is detectable in chick embryo chondrocytes, but is far less abundant than TGF-$\beta$3 mRNA in developing embryos or in chick embryo fibroblasts. TGF-$\beta$5 mRNA is expressed in frog embryos beyond the neurula state and in Xenopus tadpole (XTC) cells.

TGF-$\beta$ has been shown to have numerous regulatory actions on a wide variety of both normal and neoplastic cells. TGF-$\beta$ is multifunctional, as it can either stimulate or inhibit cell proliferation, differentiation, and other critical processes in cell function (Sporn et al., supra). For a general review of TGF-$\beta$ and its actions, see Sporn et al., *J. Cell Biol.*, 105: 1039–1045 (1987), Sporn and Roberts, *Nature*, 332: 217–219 (1988), and Roberts et al., *Recent Progress in Hormone Research*, 44: 157–197 (1988).

Natural TGF-$\beta$1 is made predominantly, if not exclusively, in a biologically latent form, which can be activated in vitro by denaturants such as urea, heat, plasmin, high salt, endoglycosidase F, capthepsin D, type IV collagenase, cocultured endothelial cells and pericytes, plasminogen activators such as urokinase, stimulated osteoclasts, or extremes of pH. See, e.g., Pircher et al., *Canc. Res.*, 44: 5538–5543 (1984) re latent TGF-$\beta$ from nontransformed and Kirsten sarcoma virus-transformed normal rat kidney cells; Antonelli-Orlidge et al., *Proc. Natl. Acad. Sci. USA*, 86: 4544–4548 (1989) re latent TGF-$\beta$ from pericytes and capillary endothelial cells; Lawrence et al., *Biochem. Biophys. Res. Commun.*, 133: 1026–1034 (1985) re latent TGF-$\beta$ from chicken embryo fibroblasts; Oreffo et al., *Biochem. Biophys. Res. Commun.*, 158: 817–823 (1989) re latent TGF-$\beta$ from murine bone organ cultures; Keski-Oja et al., *J. Cell Biol.*, 107: (6 Part 3), 1988, 50a re latent TGF-$\beta$ from human lung adenocarcinoma cell line; Miyazono and Heldin, *J. Cell. Biochem. SuDD.* 0 (13 part B) 1989, p. 92 and Miyazono and Heldin, *Nature*, 338: 158–160 (1989) re latent TGF-$\beta$ from human platelets and its carbohydrate structure; and Pircher et al., *Biochem. Biophys. Res. Commun.*, 136: 30–37 (1986) re latent TGF-$\beta$ from human blood platelets. See also Lawrence et al., *J. Cell. Physiol.*, 121: 184–188 (1984); Kryceve-Martinerie et al., *Int. J. Cancer*, 35: 553–558 (1985); Brown et al., "TGF-$\beta$", N.Y. Acad. Sci. Meeting Abstract, May 18–20, 1989; Danielpour et al., *J. Cell. Physiol.*, 138: 79–86 (1989); Wakefield et al., *J. Biol. Chem.*, 263: 7646–7654 (1988); and Miyazono et al., *J. Biol. Chem.*, 263: 6407–6415 (1988).

Several groups have characterized the latent form of TGF-$\beta$1 secreted by human platelets. Pircher et al., supra, stated that it has an apparent molecular weight of 400 Kd. More recently, it has been characterized as a three-component complex of about 235 Kd, wherein the active TGF-$\beta$1 (25 Kd dimer) is non-covalently associated with the remainder of the processed precursor (75 Kd dimer), which in turn is disulfide-bonded to an unrelated protein of 125–160 Kd (Wakefield et al., *J. Biol. Chem.*, 263, supra; Miyazono et al., supra; Miyazono et al., *J. Cell Biochem. Supp.*, 0 (12 part A), 1988, p. 200;

Wakefield et al., *J. Cell. Biochem. Suppl.*, 11A: 0, 46 (1987)).

The function of the binding protein of 125-160 Kd remains to be elucidated. Recent characterizations indicate that it contains at least 14 EGF-like repeats and six potential N-glycosylation sites and calcium binding domains (Kanzaki et al., "TGF-β", N.Y. Acad. Sci. meeting abstract, May 18-20, 1989; Miyazono, "TGF-β", N.Y. Acad. Sci. meeting abstract, May 18-20, 1989). Latent TGF-β secreted by many cells in culture has a similar structure (Wakefield et al., *J. Biol. Chem.*, supra), and this is the form in which TGF-β1 is probably perceived initially by target cells in vivo. It has been suggested that the precursor remainder of TGF-β may have an important independent biological function based on conservation of sequences in the precursor region (Roberts et al., *Recent Progress in Hormone Research*, supra). Additionally, a mutation at position 33 of precursor TGF-β1 is reported to increase the yield of mature TGF-β1, and dimerization of the precursor "pro" region is suggested as necessary to confer latency (Brunner et al., *J. Biol. Chem.*, 264: 13660-13664 (1989)).

Normal repair of tissue is a complex, sequential process involving many cell types. Fibroblasts, inflammatory cells, and keratinocytes all function in an integrated manner to promote cell division, differentiation, and migration. These processes in turn lead to enhanced connective tissue deposition and angiogenesis. Recent data suggest that these processes may be mediated both in an autocrine and paracrine manner by peptide growth factors such as TGF-β (Postlethwaite et al., *J. Exp. Med.*, 165: 251-256 (1987); Assoian et al., *Nature*, 308: 804-806 (1984)). Levels of endogenous TGF-β have been reported to increase transiently in wound chambers of the rat (Cromack et al., *J. Surg. Res.*, 42: 622-628 (1987)). Also, a crude extract of platelets containing multiple growth factors promoted healing of chronic skin ulcers (Knighton et al., *Ann Surg.*, 204: 322-330 (1986)). The results of these studies indirectly support the hypothesis that normal healing is mediated by locally produced peptide growth factors.

In vivo, TGF-β1 causes granulation tissue to form when injected intradermally (Roberts et al., *Proc. Nat. Acad. Sci. USA*, 83: 4167-4171 (1986); Sporn et al., *Science*, 219: 1329-1331 (1983)). In vitro, TGF-β1 stimulates the expression of fibronectin and collagen type I, in part mediated via increased levels of mRNA, and increases the deposition of fibronectin into the pericellular matrix (Wrana et al., *Eur. J. Biochem.*, 159: 69-76 (1986); Ignotz and Massague, *J. Biol. Chem.*, 261: 4337-4345 (1986); Fine and Goldstein, *J. Biol. Chem.*, 262: 3897-3902 (1987); Ignotz et al., *J. Biol. Chem.*, 262: 6443-6446 (1987); Raghow et al., *J. Clin. Invest.*, 79: 1285-1288 (1987); Varga and Jimeniz, *Biochem. Biophys. Res. Commun.* 138: 974-980 (1986)).

A single application of TGF-β in collagen vehicle to incisions in normal rats significantly increased tensile strength compared with untreated or collagen vehicle treated incisions (Mustoe et al., *Science*, 237: 1333-1336 (1987)). See also Brown et al., *Ann. Surg.*, 208: 788-794 (1988). In another study it was reported that TGF-β treatment reversed doxorubicin depressed uptake of hydroxyproline and thymidine in wound chambers in rats, suggesting that TGF-β might enhance the strength of the incisions by stimulating proliferation of cells and enhancing collagen synthesis (Grotendorst et al., *J. Clin. Invest.*, 76: 2323-2329 (1985)).

These results were extended using an animal model that more closely approximates healing of surgical incisions (Curtsinger et al., *Surgery, Gynecology & Obstetrics*, 168: 517-522 (1989)). It was hypothesized that because TGF-β is a potent chemoattractant for human fibroblasts (Postlethwaite et al., supra,) and stimulates collagen synthesis in cultures of renal fibroblasts in rats (Roberts et al., *Proc. Natl. Acad. Sci. USA*, supra), it may increase tensile strength by directly stimulating production of collagen by fibroblasts or by attracting inflammatory cells that may release peptide growth factors into the wounded area (Madtes et al., *Cell*, 53: 285-293 (1988); Morhenn, *Immunol. Today*, 9: 104-107 (1988)).

In addition to the scientific literature, the patent literature has also disclosed that TGF-β is useful in treating existing traumata when administered systemically or applied topically to the traumatized tissue, with promotion of rapid proliferation of cells, particularly fibroblast cells (see, e.g., EP 128,849; EP 105,014; U.S. Pat. Nos. 4,843,063; 4,774,322; 4,774,228; and 4,810,691). There is, however, also a need for an agent that predisposes mammals to accelerated tissue repair before the mammals have been subjected to trauma.

Accordingly, it is an object of the present invention to provide a method for treating mammals that have not yet experienced tissue damage to promote accelerated proliferation of the cells surrounding the traumata and consequently rapid healing.

This object and other objects will become apparent to one of ordinary skill in the art.

SUMMARY OF THE INVENTION

This invention provides a method of predisposing a mammal to accelerated tissue repair comprising systemically administering to the mammal, prior to its exposure to tissue damage, an effective amount of TGF-β. Preferably, the TGF-β is administered no more than about 24 hours prior to the tissue damage exposure. More preferably, the TGF-β is administered within a time range of from about 24 hours to greater than about 5 minutes before exposure to tissue damage.

Surprisingly, it has been found that administration of a single dose of TGF-β systemically to a mammal at least 24 hours in advance of wounding accelerates healing of the wound dramatically. This discovery was particularly surprising because TGF-β has a circulating half-life in plasma of only about 5 minutes.

DESCRIPTION OF THE PREFERRED EMBODIMENTS

A. Definitions

As used herein, the term "TGF-$\beta$" refers to the family of molecules described hereinabove, having the full-length, native amino acid sequence of any of the TGF-$\beta$s from any species. Reference to such TGF-$\beta$ herein will be understood to be a reference to any one of the currently identified forms, including TGF-$\beta$1, TGF-$\beta$2, TGF-$\beta$3, TGF-$\beta$4, and TGF-$\beta$5 (whose sequences are shown in FIG. 1), as well as to TGF-$\beta$ species identified in the future, including polypeptides derived from the sequence of any known TGF-$\beta$ and identical at 75% or more of the residues, their alleles, and their predetermined amino acid sequence variants, so long as they are effective in the method described herein. The specific terms "TGF-$\beta$1," "TGF-$\beta$2," and "TGF-$\beta$3" refer to the TGF-$\beta$s defined in the literature, e.g., Derynck et al., *Nature*, supra, Seyedin et al., *J. Biol. Chem.*, 262, supra, and deMartin et al., supra. In addition, the TGF-$\beta$ is suitably useful in the latent form or as an associated or unassociated complex of precursor and mature TGF-$\beta$.

Members of the TGF-$\beta$ family are defined as those which have nine cysteine residues in the mature portion of the molecule, share at least 65% sequence identity with other known TGF-$\beta$ sequences in the mature region, and may compete for the same receptor. In addition, they all appear to be encoded as a larger precursor that shares a region of high homology near the N-terminus and shows conservation of three cysteine residues in the portion of the precursor that will later be removed by processing. Moreover, the TGF-$\beta$s appear to have a processing site with four or five basic amino acids.

The TGF-$\beta$ is appropriately from any source, preferably mammalian, and most preferably human. TGF-$\beta$ from animals other than humans, for example, porcine or bovine sources, can be used for treating humans. Likewise, if it is desirable to treat other mammalian species such as domestic, farm, zoo, sports, or pet animals, human TGF-$\beta$, as well as TGF-$\beta$ from other species, is suitably employed.

As used herein, the term "tissue damage" refers to any form of damage or trauma to soft or hard tissue, including thermally and/or mechanically induced trauma as well as damage caused by inflammatory, infectious, and immune responses. Examples of tissue damage include surgical incisions, such as internal and epidermal surgical incisions, and corneal surgery; burns, whether first, second, or third degree; bone damage such as bone fractures, bony defects, and prosthetic implants, including injury attendant surgery such as hip replacements; wounds, including lacerations, incisions, and penetrations; sites of expected development of ulcers such as, e.g., diabetic, dental, haemophiliac, varicose, or decubitus ulcers; chronic conditions or ulcers converted to acute wounds, preferably by surgery; infections of the bone such as osteomyolitis; and any inflammatory or immune response of soft tissue such as that seen with rheumatoid arthritis or any inflammatory condition leading to bone loss, whether infectious or non-infectious.

B. Modes for Carrying Out the Invention

The method of this invention involves systemic administration to a mammal, including domestic, farm, zoo, sports, or pet animals, but preferably a human, of an effective amount of TGF-$\beta$ as an agent that predisposes the tissue to accelerated repair.

The types of patients that may be treated by the method of this invention include not only those who do or would be expected to undergo normal tissue repair, but also those that would be predicted to or do exhibit abnormal tissue repair. Impaired wound healing has many causes, including diabetes, uremia, malnutrition, vitamin deficiencies, and systemic treatment with corticosteroids, radiation, or antineoplastic agents such as doxorubicin. Thus, this invention contemplates treatment of the latter as well as the former types of patients.

The TGF-$\beta$ molecule will be formulated and dosed in a fashion consistent with good medical practice taking into account the specific tissue involved, the condition of the individual patient, the site of delivery of the TGF-$\beta$, the method of administration, and other factors known to practitioners. Thus, for purposes herein, the "therapeutically effective amount" of the TGF-$\beta$ is an amount that is effective to accelerate tissue repair in a mammal that undergoes tissue damage after administration of the TGF-$\beta$.

The TGF-$\beta$ is prepared for storage or administration by mixing TGF-$\beta$ having the desired degree of purity with physiologically acceptable carriers, excipients, or stabilizers. Such materials are non-toxic to recipients at the dosages and concentrations employed. If the TGF-$\beta$ is water soluble, it may be formulated in a buffer such as acetate or other organic acid salt, preferably at a pH of about 5 to 6. If a TGF-$\beta$ variant is only partially soluble in water, it may be prepared as a microemulsion by formulating it with a nonionic surfactant such as Tween, Pluronics, or polyethylene glycol (PEG), e.g., Tween 80, in an amount of 0.04–0.05% (w/v), to increase its solubility. Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; amino acids, such as glycine, glutamic acid, aspartic acid, or arginine; chelating agents such as EDTA; and sugar alcohols such as mannitol or sorbitol.

The TGF-$\beta$ to be used for therapeutic administration must be sterile. Sterility is readily accomplished by filtration through sterile filtration membranes (e.g., 0.2 micron membranes). The TGF-$\beta$ ordinarily will be stored in lyophilized form or as an aqueous solution since it is highly stable to thermal and oxidative denaturation. The pH of the TGF-$\beta$ preparations typically will be about 5, although higher or lower pH values may also be appropriate in certain instances. It will be understood that use of certain of the foregoing excipients, carriers, or stabilizers will result in the formation of salts of the TGF-$\beta$.

Therapeutic compositions containing the TGF-$\beta$ generally are placed into a container having a sterile access port, for example, an intravenous solution bag or vial having a stopper pierceable by a hypodermic injection needle.

Sustained release formulations may also be prepared, and include the formation of microcapsular particles and implantable articles. For preparing sustained-release TGF-$\beta$ compositions, the TGF-$\beta$ is preferably incorporated into a biodegradable matrix or microcapsule. A suitable material for this purpose is a polylactide, although other polymers of poly-($\alpha$-hydroxycarboxylic acids), such as poly-D-(-)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the condition. This can be determined by routine screening in representative animal models such as impaired rat skin linear incision models, or, if such models are unavailable, in normal animals.

For examples of sustained release compositions, see U.S. Pat. No. 3,773,919, EP 58,481A, U.S. Patent No. 3,887,699, EP 158,277A, Canadian Patent No. 1176565, U. Sidman et al., *Biololymers*, 22: 547 (1983), and R. Langer et al., *Chem. Tech.*, 12: 98 (1982).

Tissue damage caused by infections may be treated with TGF-$\beta$ formulated with an effective amount of an antibiotic such as cephalosporin or penicillin. Alternatively, the antibiotic and C TGF-$\beta$ may be administered separately to the patient using the general methods described above. The treating physician will be able to determine the proper dosages and administration routes of antibiotic based on conventional therapy for treating infectious conditions.

The dosage of TGF-$\beta$ to be employed is dependent upon the factors described above, especially the type of tissue damage which is expected. As a general proposition, a dose of about 0.015 to 5 mg/kg, preferably to 0.5 mg/kg, of TGF-$\beta$ may be administered to the patient, whether via, e.g., one or more single administrations, continuous infusion, or bolus injection. The advantage of this invention lies in the use of only one administration of TGF-$\beta$, preferably intravenously, so one dose is preferred. However, other dosage regimens may be useful. This administration takes place prior to infliction of damage to the tissue, e.g., before surgery, preferably no more than about 24 hours before tissue damage is inflicted, and more preferably from within 24 hours to greater than about 5 minutes prior to tissue damage.

The invention is more fully illustrated in the example set forth below, which is intended to represent one embodiment of the invention, but not the only embodiment. All references to literature or patent applications herein are expressly incorporated herein by reference.

EXAMPLE I

Material: Recombinant human TGF-$\beta$1 was cloned (Derynck et al., *Nature*, supra) and expressed in Chinese hamster ovary cells (using a method such as that described by Graycar et al., *Molecular Endocrinology*, 3: 1977-1986 (1989) and U.S pat. No. 4,886,747 issued Dec. 12, 1989). The protein was purified by harvesting the cell culture fluid, concentrating this fluid with a Pellicon cassette system, diluting the concentrate with three vols. of a mixture of 50:1 of reagent alcohol to HCl, allowing the mixture to sit for 1 hour at 4° C., adjusting the pH to 7.5-8, centrifuging the mixture, loading the supernatant on a cation exchange S Sepharose Fast Flow column (previously equilibrated with 6M urea, 20 mM MOPS buffer, pH 8), washing the column with the same buffer, eluting with a gradient of 0 to 0.4M sodium chloride in the same buffer, making a pool from the gradient fractions run on a gel, adjusting the pH of the pool to 4.5, applying the pool to a second cation-exchange SP Toyopearl column previously equilibrated in 2M urea, 50 mM sodium acetate buffer at pH 4.5, washing the column with the same buffer, eluting with a gradient of 0 to 1M sodium chloride in the same buffer, making a pool from the gradient fractions run on a gel, concentrating the pool on a stirred cell Amicon concentrator, loading the concentrate on a HW55S Toyopearl gel filtration column, washing with 1M acetic acid, making a pool from the gradient fractions run on a gel, and exchanging the pool into 20 mM sodium acetate buffer at pH 5 over Cellufine GH-25.

Vehicle (saline) was formulated in the sodium acetate buffer at pH 5 without the TGF-$\beta$1. The material was stored at 4° C. until use.

Animal Surgery: Adult male Sprague Dawley rats, 300-350 grams (Charles River Laboratories, Wilmington, Mass.), maintained in accordance with guidelines from the NIH and the American Association for the Accreditation of Laboratory Animal Care, were anesthetized by an intramuscular injection of ketamine hydrochloride/xylazine hydrochloride/acetylpromazine maleate mixture. The hair was clipped from the back and sides and disinfected with betadine and 70% alcohol rinse. At this time each rat was given a single intravenous (iv) injection of either saline or one of four concentrations of TGF-$\beta$1 at a volume of 1.0 ml/kg. After injection of vehicle or TGF-$\beta$1, two pairs of symmetrical transverse full-thickness skin incisions approximately 2.5 cm in length were made by cutting through the subdermal panniculus carnosus musculature. Each wound was closed with two interrupted 4-0 stainless steel sutures evenly divided across the wound. After surgery each rat was administered either a single intramuscular injection of 5 mg methylprednisolone to inhibit inflammation and thus impair the healing process or saline to serve as an unimpaired healing control. The animals were returned to their cages and allowed to recover.

Additional animals were treated in an identical manner with the exception of a single intravenous dose of TGF-$\beta$1 administered 24, 48, or 72 hours before surgery rather than at the time of surgery.

Tissue Sampling: In a time-dependent manner rats were euthanized and 1-2 mm cross-sections of the wound from the center of each scar were removed with samples fixed in 10% neutral buffered formalin for light microscopic examination and Karnovsky's solution for electron microscopy. Two 8×25 mm samples from each wound were removed and fixed in 10% formalin for seven days for wound strength determinations.

Tensometry: Tissues were uniformly trimmed in width and length (8 mm × 25 mm) to assure that the edges of the scar were exposed on both sides of the sample. Tensometry was performed on coded samples using a calibrated tensometer (Instron Universal Testing Instrument Model 1011, Instron Corp., Canton, Mass.). The value determined was breaking strength (g), which is a measure of force in grams applied to the tissue at the point where the scar tissue visually breaks and a major deflection occurs in the tracing.

Figure 2:
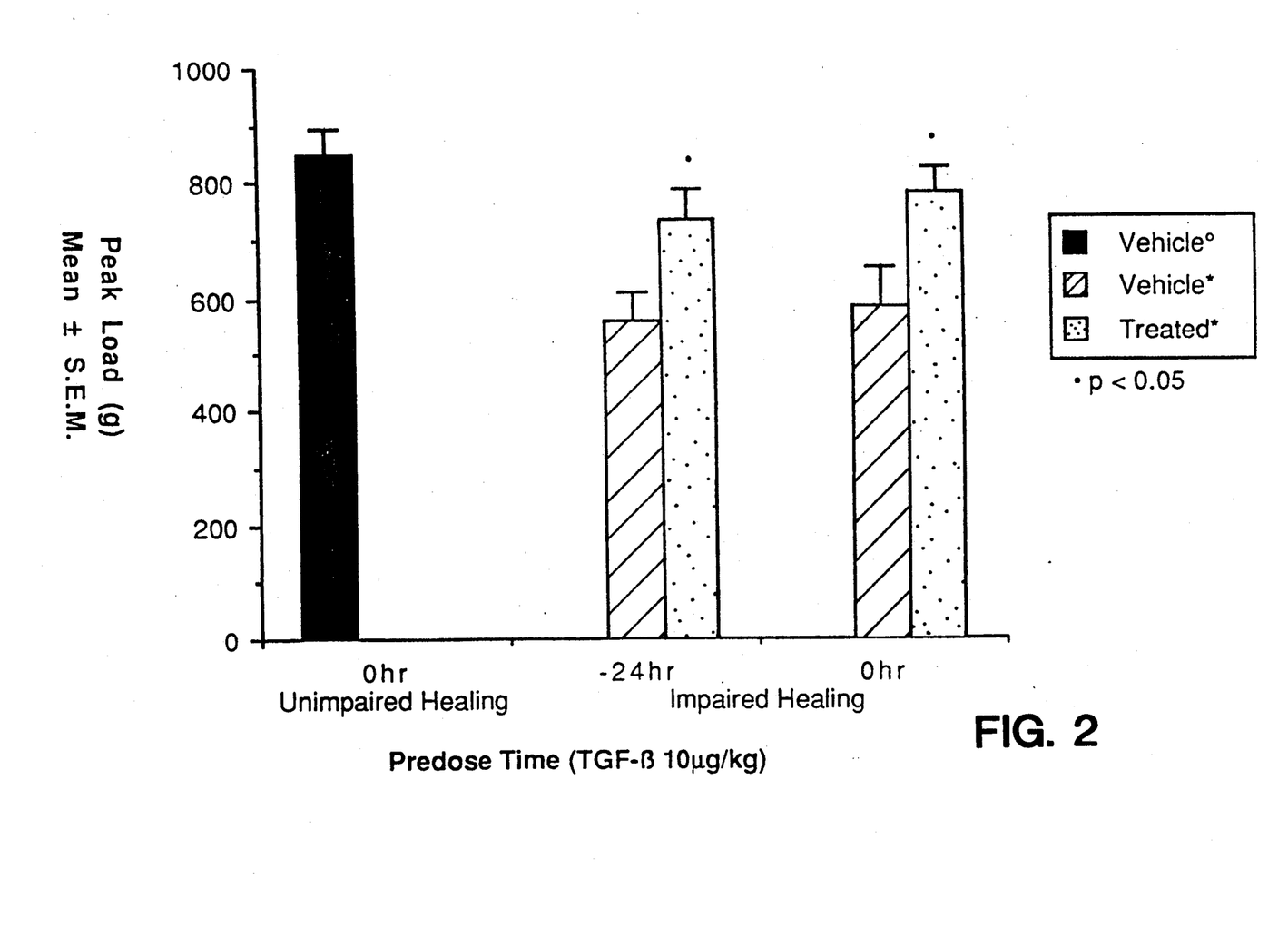
FIG. 2 represents the peak load, which is a measure of strength, of linear skin incision wounds. Rats were treated intramuscularly with 5 mg prednisolone (asterisk) at the time of wounding to impair healing processes or treated with saline (black) as an unimpaired-healing control. Saline (diagonal stripes) or 10 μg/kg rhTGF-β1 (cross-hatching) was administered intravenously 24 hours before (−24 hr.) or at the time of (0 hr.) wounding.

Results: Two separate studies were performed in which there were an unimpaired-healing control (saline) group and an impaired-healing control (saline) group and TGF-$\beta$1-treated group(s). The first study compared the effects of 10 $\mu$g/kg TGF-$\beta$1 to saline control when administered intravenously either 24 hours prior to or just before skin incision. Results of this study are presented in FIG. 2 and indicate that wounds treated with 10 $\mu$g/kg TGF-$\beta$1 exhibited increased strength ($p<0.05$) compared to its concurrent vehicle control. In addition, the impaired-healing wounds treated with TGF-$\beta$1 were approximately 90% as strong as unimpaired-healing wounds treated with vehicle.

Figure 3:
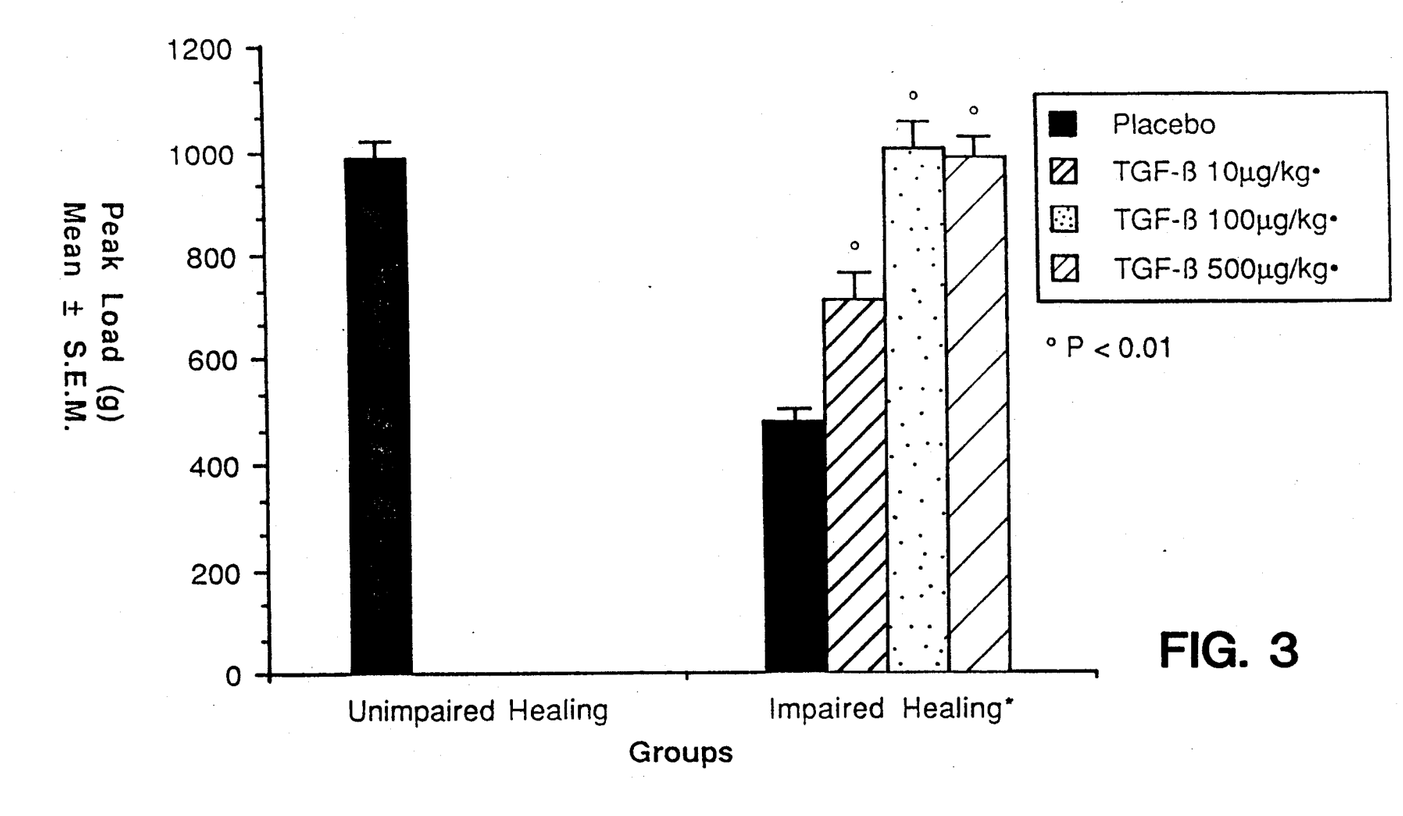
FIG. 3 represents the peak load of the impaired-healing rat skin linear incision wounds treated intravenously with saline (black) or with 10 μg/kg, 100 μg/kg, or 500 μg/kg of rhTGF-β1 and intramuscularly with 5 mg methylprednisolone at the time of wounding. A group treated with saline but not treated with methylprednisolone served as an unimpaired-healing control.

The second study was identical in design with the addition of 100 μg/kg and 500 μg/kg doses of TGF-β1, Results, presented in FIG. 3, indicate that all three dose levels of TGF-β1 increased the strength of linear incision wounds compared with impaired-healing vehicle control (p<0.01). Both the 100 and 500 μg/kg doses of TGF-β1 returned impaired-healing wounds to the same strength as unimpaired-healing vehicle treated wounds (FIG. 3).

Thus, TGF-β is effective when administered as single iv doses of 10 to 500 μg/kg in accelerating wound healing in this model. This model is predictive of the results that one would obtain in a clinical trial.

What is claimed is:

1. A method of predisposing a mammal to accelerated tissue repair comprising systematically administering to the mammal, within a time range of from about 24 hours to greater than about 5 minutes prior to tissue damage exposure, an effective amount of TGF-β.

2. The method of claim 1 wherein the administration is in a single dose.

3. The method of claim 1 wherein the administration is intravenous.

4. The method of claim 1 wherein the TGF-β is human TGF-β.

5. The method of claim 4, wherein the TGF-β is TGF-β1.

6. The method of claim 1 wherein the mammal is human.

7. The method of claim 1 wherein the tissue repair is wound healing and the tissue damage is a wound.

8. The method of claim 1 wherein the tissue repair is bone repair and the tissue damage is a bone fracture, prosthetic implant, or bony defect.

9. The method of claim 1 wherein the tissue damage is surgical incision.

* * * * *

UNITED STATES PATENT AND TRADEMARK OFFICE
CERTIFICATE OF CORRECTION

PATENT NO. : 5,108,989

DATED : 28 April 1992

INVENTOR(S) : EDWARD P. AMENTO ET AL.

It is certified that error appears in the above-identified patent and that said Letters Patent is hereby corrected as shown below:

In column 9, line 19, change "systematically" to "systemically".

Signed and Sealed this

Twenty-eighth Day of September, 1993

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,108,989
DATED : April 28, 1992
INVENTOR(S) : AMENTO and BECK

Figure 1A:
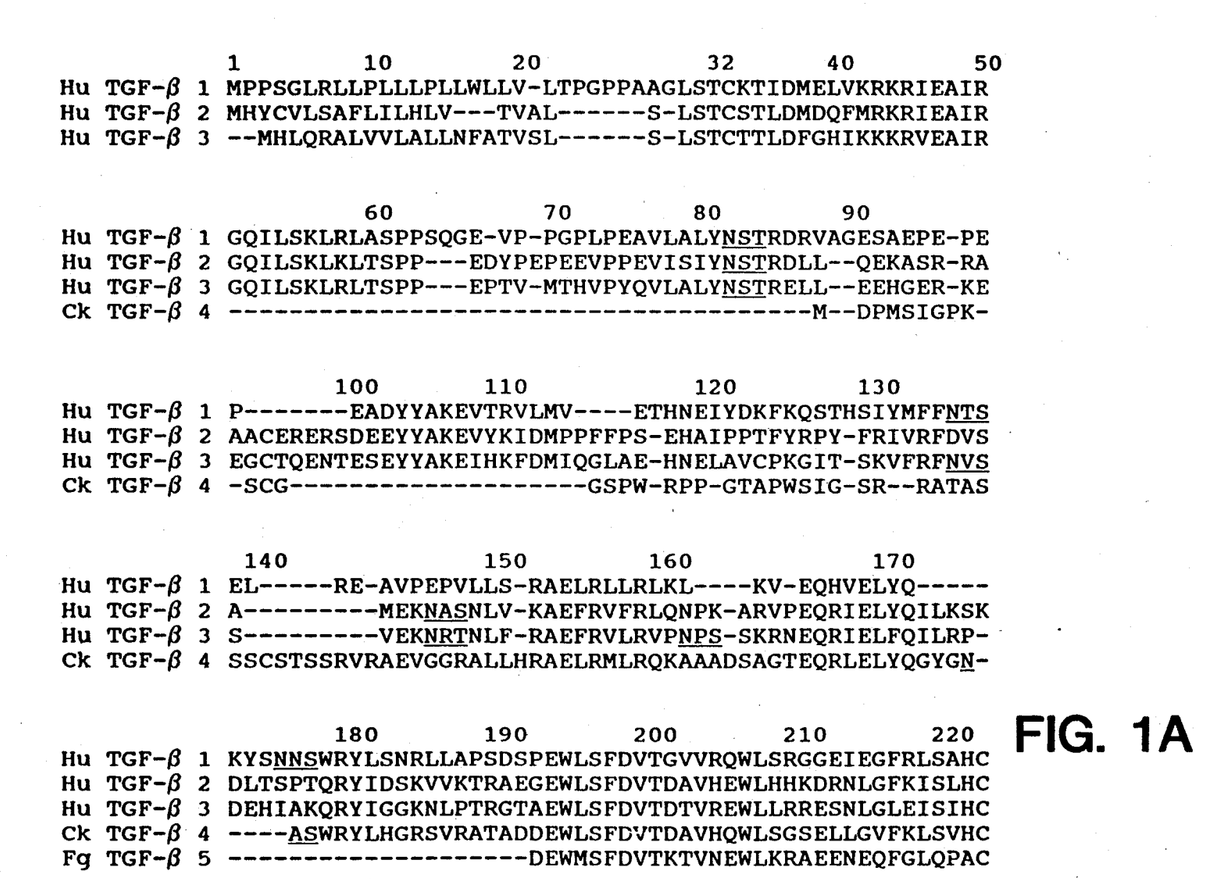
FIG. 1 depicts the sequences of human TGF-β1, human TGF-β2, human TGF-β3, chick TGF-β4, and frog TGF-β5.
Figure 1B:
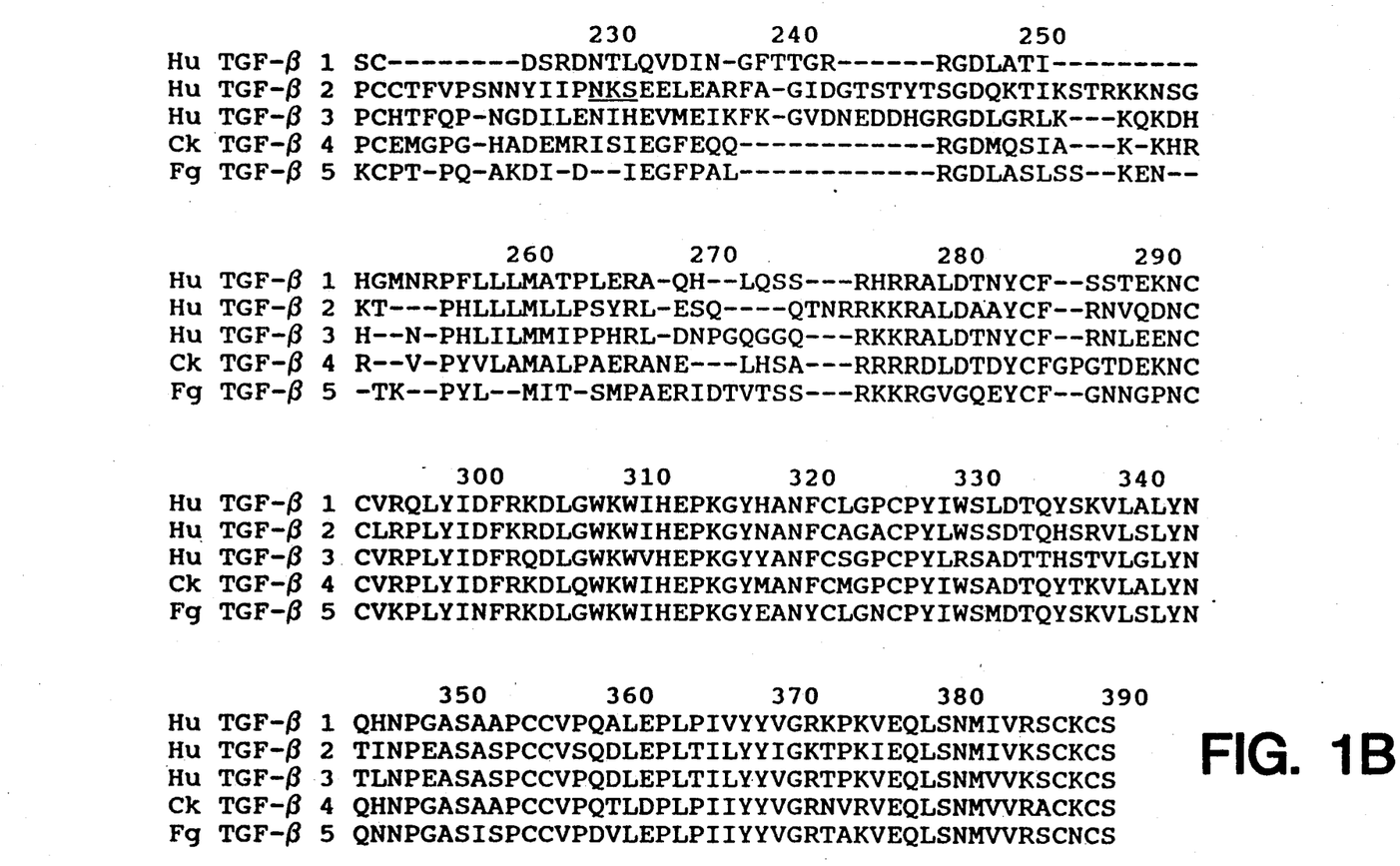

It is certified that error appears in the above-indentified patent and that said Letters Patent is hereby corrected as shown below:

IN THE DRAWINGS:

In Figure 1A, line 3, please delete "Hu TGF-β 3 --" and replace it as follows: --Hu TGF-β 3 MK--.

Signed and Sealed this

Thirtieth Day of January, 1996

*Attest:*

BRUCE LEHMAN

*Attesting Officer*  Commissioner of Patents and Trademarks